United States Patent
Amschler et al.

(10) Patent No.: US 11,100,250 B2
(45) Date of Patent: Aug. 24, 2021

(54) CONTROLLING ACCESS TO DATA IN A HEALTH NETWORK

(71) Applicant: PHILIPS HEALTHCARE INFORMATICS, INC., Cambridge, MA (US)

(72) Inventors: John Earl Amschler, San Diego, CA (US); Soumya Das, San Diego, CA (US)

(73) Assignee: Philips Healthcare Informatics, Inc., Cambridge, MA (US)

( * ) Notice: Subject to any disclaimer, the term of this patent is extended or adjusted under 35 U.S.C. 154(b) by 0 days.

(21) Appl. No.: 15/695,901

(22) Filed: Sep. 5, 2017

(65) Prior Publication Data
US 2019/0073489 A1    Mar. 7, 2019

(51) Int. Cl.
*G06F 21/62* (2013.01)
*H04L 9/32* (2006.01)
(Continued)

(52) U.S. Cl.
CPC ........ *G06F 21/6245* (2013.01); *A61B 5/0022* (2013.01); *A61B 5/0024* (2013.01); *G16H 10/60* (2018.01); *G16H 40/63* (2018.01); *H04L 9/0643* (2013.01); *H04L 9/0833* (2013.01); *H04L 9/0861* (2013.01); *H04L 9/14* (2013.01); *H04L 9/3236* (2013.01); *H04L 63/065* (2013.01); *H04L 63/105* (2013.01); *A61B 5/01* (2013.01); *A61B 5/021* (2013.01); *A61B 5/02438* (2013.01); *A61B 5/0816* (2013.01); *A61B 5/14532* (2013.01); *A61B 5/14551* (2013.01); *A61B 5/318* (2021.01); *A61B 5/6823* (2013.01);
(Continued)

(58) Field of Classification Search
CPC ..... G06F 21/6245; H04L 9/0463; H04L 9/14; H04L 9/3236; H04L 63/065; H04L 63/105
See application file for complete search history.

(56) References Cited

U.S. PATENT DOCUMENTS

| | | | |
|---|---|---|---|
| 5,809,148 A * | 9/1998 | Doberstein | H04L 9/0637 380/262 |
| 6,704,871 B1 * | 3/2004 | Kaplan | G06F 21/72 713/192 |

(Continued)

FOREIGN PATENT DOCUMENTS

EP    2 330 771 A2    6/2011

OTHER PUBLICATIONS

NPL Search (Google Scholar) (Year: 2021).*
(Continued)

*Primary Examiner* — Mahfuzur Rahman
*Assistant Examiner* — Richard W Cruz-Franqui

(57) ABSTRACT

Some methods may involve receiving, at a first node of the health network, encrypted sensor data from one or more sensors. The first node may be in a data communication path between the one or more sensors and other nodes of the health network. The method may involve decrypting, by the first node of the health network, only a portion of the encrypted sensor data, and transmitting the encrypted sensor data from the first node of the health network to a second node of the health network. The first node may be a gateway device. In some examples, the second node may be able to decrypt more of the encrypted sensor data than the first node.

30 Claims, 4 Drawing Sheets

(51) Int. Cl.

| | | |
|---|---|---|
| H04L 29/06 | (2006.01) | |
| H04L 9/14 | (2006.01) | |
| H04L 9/06 | (2006.01) | |
| G16H 10/60 | (2018.01) | |
| A61B 5/00 | (2006.01) | |
| H04L 9/08 | (2006.01) | |
| G16H 40/63 | (2018.01) | |
| A61B 5/021 | (2006.01) | |
| A61B 5/145 | (2006.01) | |
| A61B 5/1455 | (2006.01) | |
| A61B 5/024 | (2006.01) | |
| A61B 5/01 | (2006.01) | |
| A61B 5/08 | (2006.01) | |
| A61B 5/318 | (2021.01) | |

(52) U.S. Cl.
CPC ....... *A61B 5/6824* (2013.01); *H04L 2209/805* (2013.01); *H04L 2209/88* (2013.01)

(56) References Cited

U.S. PATENT DOCUMENTS

| | | | | |
|---|---|---|---|---|
| 7,478,434 | B1* | 1/2009 | Hinton | G06F 16/958 726/27 |
| 7,539,313 | B1* | 5/2009 | Hardjono | H04L 63/064 380/278 |
| 7,593,529 | B1* | 9/2009 | Yang | H04N 7/1675 380/200 |
| 7,792,292 | B2* | 9/2010 | Matsushima | H04N 5/91 380/200 |
| 7,849,306 | B2 | 12/2010 | Takeshima et al. | |
| 8,126,728 | B2 | 2/2012 | Dicks et al. | |
| 8,645,716 | B1* | 2/2014 | Dujari | G06F 21/71 713/193 |
| 8,788,805 | B2 | 7/2014 | Herne et al. | |
| 9,027,143 | B1* | 5/2015 | Agrawal | G06F 21/51 726/26 |
| 9,626,359 | B1* | 4/2017 | Sun | G06F 40/40 |
| 9,723,433 | B2* | 8/2017 | Masoud | G06F 21/30 |
| 2002/0129243 | A1* | 9/2002 | Nanjundiah | H04N 21/23476 713/160 |
| 2006/0129805 | A1* | 6/2006 | Kim | H04L 9/0869 713/158 |
| 2008/0075291 | A1* | 3/2008 | Kamijoh | H04L 9/0836 380/279 |
| 2008/0097912 | A1* | 4/2008 | Dicks | G16H 40/67 705/50 |
| 2008/0218311 | A1* | 9/2008 | Pless | G06K 7/01 340/5.81 |
| 2008/0256356 | A1* | 10/2008 | Iyengar | H04L 9/0836 713/155 |
| 2008/0263370 | A1 | 10/2008 | Hammoutene et al. | |
| 2010/0020966 | A1* | 1/2010 | Hata | H04L 9/0861 380/44 |
| 2010/0180116 | A1* | 7/2010 | Coan | H04L 9/0891 713/168 |
| 2012/0022387 | A1* | 1/2012 | Baida | A61B 5/339 600/523 |
| 2013/0132729 | A1* | 5/2013 | Arnold | G09C 5/00 713/176 |
| 2013/0231947 | A1* | 9/2013 | Shusterman | A61B 5/02055 705/2 |
| 2013/0247090 | A1* | 9/2013 | Kummer | H04N 21/4181 725/31 |
| 2014/0033247 | A1* | 1/2014 | Wingert | H04N 21/435 725/31 |
| 2015/0324605 | A1* | 11/2015 | Yoon | G06F 21/62 726/28 |
| 2015/0326393 | A1* | 11/2015 | Takashima | H04N 21/8358 380/30 |
| 2016/0232010 | A1* | 8/2016 | Dicks | G06F 8/654 |
| 2016/0232322 | A1* | 8/2016 | Mensinger | A61B 5/7275 |
| 2016/0330573 | A1* | 11/2016 | Masoud | G06F 21/606 |
| 2016/0331233 | A1* | 11/2016 | Mensinger | H04L 43/065 |
| 2017/0026414 | A1 | 1/2017 | Frydman et al. | |
| 2017/0078101 | A1* | 3/2017 | Maximov | H04L 9/3247 |
| 2017/0103228 | A1* | 4/2017 | Yavuz | H04L 9/083 |
| 2017/0140146 | A1* | 5/2017 | Mehta | G06F 21/6218 |
| 2018/0183772 | A1* | 6/2018 | Jeon | H04L 63/12 |
| 2019/0073489 | A1* | 3/2019 | Amschler | H04L 9/0833 |
| 2019/0339688 | A1* | 11/2019 | Celia | G05B 19/41865 |

OTHER PUBLICATIONS

Abid Ramin, et al., "Design and Implementation of a Low Cost Wireless Sensor Network using Arduino and nRF24L01(+)," IJARCCE, vol. 5, issue 5, May 2016, pp. 307-309, XP055511468, DOI: 10.17148/IJARCCE.2016.5869 Retrieved from the Internet: URL:http://www.ijsret.org/pdf/121571.pdf.

Hu Bin et al., "Smart Grid Mesh Network Security Using Dynamic Key Distribution With Merkle Tree 4-Way Handshaking", IEEE Transactions on Smart Grid, IEEE, USA, vol. 5, No. 2, Mar. 1, 2014, pp. 550-558, XP011540049, ISSN: 1949-3053, DOI: 10.1109/TSG.2013.2277963.

Sherman A. T. et al., "Key Establishment in Large Dynamic Groups Using One-Way Function Trees", IEEE Transactions on Software Engineering, IEEE Service Center, Los Alamitos, CA, US, vol. 29, No. 5, May 1, 2003, pp. 444-458, XP002996771, ISSN: 0098-5589.

"Key Establishment in Large Dynamic Groups Using One-Way Function Trees", Key Establishment in Large Dynamic Groups Using One-Way Functiontrees, XX, XX, May 20, 1998, pp. 1-13, XP002126220.

International Search Report and Written Opinion for PCT/US2018/044083 dated Oct. 12, 2018, all pages.

PCT/US2018/044083, "International Preliminary Report on Patentability", dated Mar. 19, 2020, 8 pages.

* cited by examiner

CONTROLLING ACCESS TO DATA IN A HEALTH NETWORK

TECHNICAL FIELD

This disclosure relates generally to methods and devices for controlling access to data in a health network.

DESCRIPTION OF THE RELATED TECHNOLOGY

Although the concepts described in this document apply generally to various health-related devices and networks, some examples will be described in the context of Qualcomm's 2net "ecosystem," which provides the infrastructure for a wide range of remote care use cases and can serve as part of the infrastructure for the Internet of Medical Things (IoMT). The health data sources for the 2net ecosystem may include wearable devices having sensors, implanted devices, medical devices, diagnostic devices, etc. In some examples, these health data sources (which also may be referred to herein as "sensors") may provide data to a cloud-based service platform via wireless communication with a smart phone or other gateway device. A medical provider backend system may be configured to obtain data via the service platform. For many reasons which include patient privacy, end-to-end security between the sensors and the provider backend would be desirable. The least secure link in this system is normally the wireless link between the health data sources and the gateway devices.

SUMMARY

The systems, methods and devices of the disclosure each have several innovative aspects, no single one of which is solely responsible for the desirable attributes disclosed herein.

Some innovative aspects of the subject matter described in this disclosure may be implemented in a method. For example, the method may involve controlling access to data in a health network. The method may involve receiving, at a first node of the health network, encrypted data. For example, the method may involve receiving, at the first node of the health network, encrypted sensor data from one or more sensors. In some examples, the first node may be in a data communication path between the one or more sensors and other nodes of the health network. According to some examples, the first node of the health network may be a gateway device. The method may involve decrypting, by the first node of the health network, only a portion of the encrypted sensor data.

In some alternative implementations, the method may involve receiving, at the first node of the health network, encrypted patient data that has previously been entered into a record, recorded and stored in a memory, etc. For example, the method may involve receiving, at the first node of the health network, encrypted physiological data that has previously been entered into a record, recorded and stored in a memory, etc. The physiological data may, for example, include body temperature data, respiration rate data, oxygen saturation data, blood glucose data, blood pressure data, heart rate data, data indicating electrical activity of a user's heart, actigraphy data and/or blood alcohol data. The method may involve decrypting, by the first node of the health network, only a portion of the encrypted patient data. The method may involve transmitting the encrypted patient data from the first node of the health network to a second node of the health network.

The method may involve transmitting the encrypted sensor data and/or the encrypted patient data from the first node of the health network to a second node of the health network. The second node of the health network may, in some examples, be a node of a health service provider system. The health service provider system may be operated by, and/or on behalf of, a medical group, a hospital, a retail pharmacy, a medical research laboratory, or another health-related entity.

In some implementations, the first node may include a user interface. The method may involve controlling the user interface to provide one or more indications corresponding to a decrypted portion of the encrypted sensor data and/or the encrypted patient data.

According to some examples, the first node may receive a series of encrypted sensor data transmissions from the one or more sensors. In some such examples, the first node may decrypt at least a portion of every Nth encrypted sensor data transmission but may not decrypt first through $(N-1)^{th}$ encrypted sensor data transmissions of the series of encrypted sensor data transmissions.

In other examples, the first node also may receive a series of encrypted sensor data transmissions from the one or more sensors. In some such examples, the first node may decrypt at least a portion of an encrypted sensor data transmission received after a time interval has elapsed. However, in some examples the first node may not decrypt other encrypted sensor data transmissions of the series of encrypted sensor data transmissions received before the time interval has elapsed.

In still other examples, the first node may receive a series of encrypted sensor data transmissions from the one or more sensors. In some such examples, the first node may decrypt a portion of each encrypted sensor data transmission of the series of encrypted sensor data transmissions.

In some implementations, the method may involve providing a plurality of levels of access, by nodes in the data communication path, to encrypted sensor data transmissions from the one or more sensors and/or to the encrypted patient data. According to some such implementations, the first node may have a different level of access than the second node. For example, the second node may have a higher level of access than the first node.

In some examples, a group encryption key for top-level access ($KG_t$) may be computed via a one-way hash of a root encryption key. According to some such examples, a group encryption key $KG_i$ for an $i^{th}$ level of access may be computed via a one-way hash of a group encryption key $KG_{i-1}$ for an $(i-1)^{th}$ level of access. The group encryption key $KG_i$ and the group encryption key $KG_{i-1}$ may, for example, be symmetrical encryption keys.

According to some implementations, the encrypted sensor data from the one or more sensors and/or to the encrypted patient data may include a first portion encrypted at a first level. In some such implementations, the encrypted sensor data and/or to the encrypted patient data may include second portion encrypted at a second level that is different from the first level.

Some or all of the operations, functions and/or methods described herein may be performed by one or more devices according to instructions (e.g., software) stored on non-transitory media. Such non-transitory media may include memory devices such as those described herein, including but not limited to random access memory (RAM) devices, read-only memory (ROM) devices, etc. Accordingly, some innovative aspects of the subject matter described in this disclosure can be implemented in one or more non-transitory media having software stored thereon.

For example, the software may include instructions for controlling at least a first node of a health network to perform a method. The first node may be in a data communication path between one or more sensors and other nodes of the health network.

The method may involve receiving, at a first node of the health network, encrypted data. For example, the method may involve receiving, at the first node of the health network, encrypted sensor data from one or more sensors. In some examples, the first node may be in a data communication path between the one or more sensors and other nodes of the health network. According to some examples, the first node of the health network may be a gateway device. The method may involve decrypting, by the first node of the health network, only a portion of the encrypted sensor data.

In some alternative implementations, the method may involve receiving, at the first node of the health network, encrypted patient data that has previously been entered into a record, recorded and stored in a memory, etc. For example, the method may involve receiving, at the first node of the health network, encrypted physiological data that has previously been entered into a record, recorded and stored in a memory, etc. The physiological data may, for example, include body temperature data, respiration rate data, oxygen saturation data, blood glucose data, blood pressure data, heart rate data, data indicating electrical activity of a user's heart, actigraphy data and/or blood alcohol data. The method may involve decrypting, by the first node of the health network, only a portion of the encrypted patient data. The method may involve transmitting the encrypted patient data from the first node of the health network to a second node of the health network.

The method may involve transmitting the encrypted sensor data and/or the encrypted patient data from the first node of the health network to a second node of the health network. The second node of the health network may, in some examples, be a node of a health service provider system. The health service provider system may be operated by, and/or on behalf of, a medical group, a hospital, a retail pharmacy, a medical research laboratory, or another health-related entity.

In some implementations, the first node may include a user interface. The method may involve controlling the user interface to provide one or more indications corresponding to a decrypted portion of the encrypted sensor data and/or the encrypted patient data.

According to some examples, the first node may receive a series of encrypted sensor data transmissions from the one or more sensors. In some such examples, the first node may decrypt at least a portion of every Nth encrypted sensor data transmission but may not decrypt first through $(N-1)^{th}$ encrypted sensor data transmissions of the series of encrypted sensor data transmissions.

In other examples, the first node also may receive a series of encrypted sensor data transmissions from the one or more sensors. In some such examples, the first node may decrypt at least a portion of an encrypted sensor data transmission received after a time interval has elapsed. However, in some examples the first node may not decrypt other encrypted sensor data transmissions of the series of encrypted sensor data transmissions received before the time interval has elapsed.

In still other examples, the first node may receive a series of encrypted sensor data transmissions from the one or more sensors. In some such examples, the first node may decrypt a portion of each encrypted sensor data transmission of the series of encrypted sensor data transmissions.

In some implementations, the method may involve providing a plurality of levels of access, by nodes in the data communication path, to encrypted sensor data transmissions from the one or more sensors and/or to the encrypted patient data. According to some such implementations, the first node may have a different level of access than the second node. For example, the second node may have a higher level of access than the first node.

In some examples, a group encryption key for top-level access ($KG_i$) may be computed via a one-way hash of a root encryption key. According to some such examples, a group encryption key $KG_i$ for an $i^{th}$ level of access may be computed via a one-way hash of a group encryption key $KG_{i-1}$ for an $(i-1)^{th}$ level of access. The group encryption key $KG_i$ and the group encryption key $KG_{i-1}$ may, for example, be symmetrical encryption keys.

According to some implementations, the encrypted sensor data from the one or more sensors and/or to the encrypted patient data may include a first portion encrypted at a first level. In some such implementations, the encrypted sensor data and/or to the encrypted patient data may include second portion encrypted at a second level that is different from the first level.

Some innovative aspects of the subject matter described in this disclosure may be implemented in an apparatus. The apparatus may, in some examples, be configured to function as a first node of a health network. The first node may, in some examples, be in a data communication path between one or more sensors and other nodes of the health network. The apparatus may, for example, be a gateway device of the health network. The apparatus may include an interface system and a control system that is configured for communication with the interface system.

In some implementations, the interface system may include a user interface system, one or more network interfaces, one or more interfaces between the control system and a memory system and/or one or more interfaces between the control system and one or more external device interfaces (e.g., ports or applications processors). In some examples, the interface system may include a wireless interface system.

The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. According to some examples, the interface system may be configured for receiving encrypted sensor data from the one or more sensors. In some such examples, the control system may be configured to receive, from the interface system, at least a portion of the encrypted sensor data. The control system may be configured to decrypt only the portion of the encrypted sensor data. The control system may be configured to cause the interface system to transmit the encrypted sensor data to a second node of the health network. The second node of the health network may, for example, be a node of a health service provider system.

In some alternative implementations, the interface system may be configured for receiving, at the first node of the health network, encrypted patient data that has previously been entered into a record, recorded and stored in a memory, etc. For example, the interface system may be configured for receiving encrypted physiological data that has previously been entered into a record, recorded and stored in a memory, etc. The physiological data may, for example, include body temperature data, respiration rate data, oxygen saturation data, blood glucose data, blood pressure data, heart rate data, data indicating electrical activity of a user's heart, actigraphy data and/or blood alcohol data.

In some such examples, the control system may be configured to receive, from the interface system, at least a portion of the encrypted patient data. The control system may be configured to decrypt only the portion of the encrypted patient data. The control system may be configured to cause the interface system to transmit the encrypted patient data to a second node of the health network.

In some implementations, the apparatus may include a user interface. According to some such implementations, the control system may be configured to control the user interface to provide one or more indications corresponding to a decrypted portion of the encrypted sensor data and/or a decrypted portion of the encrypted patient data.

According to some implementations, the interface system may receive a series of encrypted sensor data transmissions from the one or more sensors. In some such implementations, the control system may be configured to decrypt at least a portion of every Nth encrypted sensor data transmission. However, in some examples the control system may be configured not to decrypt first through $(N-1)^{th}$ encrypted sensor data transmissions of the series of encrypted sensor data transmissions.

According to other implementations, the interface system also may receive a series of encrypted sensor data transmissions from the one or more sensors. In some such implementations, the control system may be configured to decrypt at least a portion of an encrypted sensor data transmission received after a time interval has elapsed. However, in some examples the control system may be configured not to decrypt other encrypted sensor data transmissions of the series of encrypted sensor data transmissions received before the time interval has elapsed.

According to still other implementations, the interface system may receive a series of encrypted sensor data transmissions from the one or more sensors. In some such implementations, the control system may be configured to decrypt a portion of each encrypted sensor data transmission of the series of encrypted sensor data transmissions.

BRIEF DESCRIPTION OF THE DRAWINGS

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale. Like reference numbers and designations in the various drawings indicate like elements.

DETAILED DESCRIPTION

Figure 1:
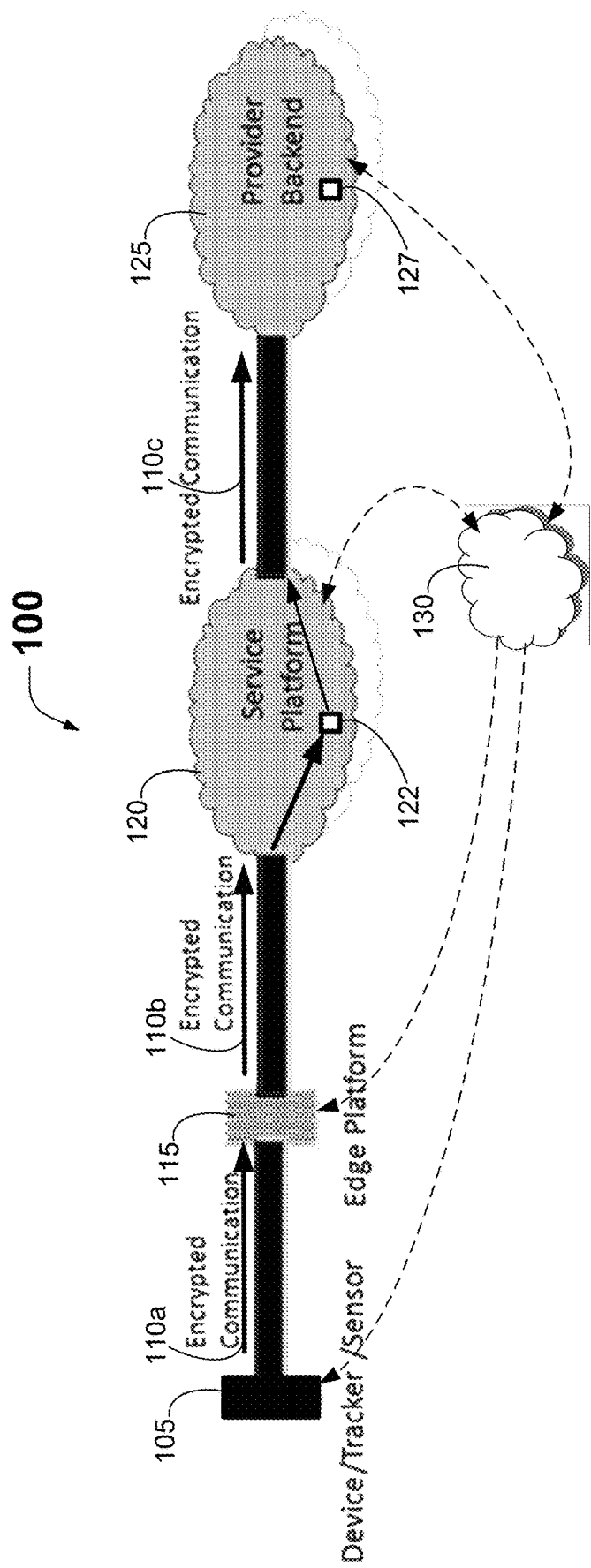
FIG. 1 is a network diagram that shows examples of components of a health network according to some disclosed implementations.

The following description is directed to certain implementations for the purposes of describing the innovative aspects of this disclosure. However, a person having ordinary skill in the art will readily recognize that the teachings herein may be applied in a multitude of different ways. The described implementations may be implemented in various other devices. In addition, it is contemplated that at least some aspects of the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, handheld or portable computers, netbooks, notebooks, smartbooks, tablets, printers, copiers, scanners, facsimile devices, global navigation satellite system (GNSS) receivers/navigators, cameras, digital media players (such as MP3 players), camcorders, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), portable memory chips, electromechanical systems (EMS) devices, including but not limited to microelectromechanical systems (MEMS) devices, etc. The teachings herein also may be used in applications such as, but not limited to, electronic switching devices, radio frequency filters, sensors, accelerometers, gyroscopes, motion-sensing devices, magnetometers, inertial components for consumer electronics, parts of consumer electronics products, steering wheels or other automobile parts, varactors, liquid crystal devices, electrophoretic devices, drive schemes, manufacturing processes and electronic test equipment. Thus, the teachings are not intended to be limited to the implementations depicted solely in the Figures, but instead have wide applicability as will be readily apparent to one having ordinary skill in the art.

Some disclosed implementations provide end-to-end security between health data sources, such as sensors, and one or more health service provider (hereinafter, "provider") backend systems of a health network. Some such devices may be used to access the network and/or provide data to the network and some such devices may form part of the health network. Some disclosed implementations may provide varying degrees of access to health data in a data communication path from health data sources, such as one or more sensors, to nodes of a health network. For example, some methods may involve receiving, at a first node of the health network, encrypted sensor data from one or more sensors. In some alternative implementations, the method may involve receiving, at the first node of the health network, encrypted patient data that has previously been entered into a record, recorded and stored in a memory, etc. For example, the method may involve receiving, at the first node of the health network, encrypted physiological data that has previously been entered into a record, recorded and stored in a memory, etc. The physiological data may, for example, include body temperature data, respiration rate data, oxygen saturation data, blood glucose data, blood pressure data, heart rate data, data indicating electrical activity of a user's heart, actigraphy data and/or blood alcohol data.

The first node may be in a data communication path between the one or more sensors and other nodes of the health network. The method may involve decrypting, by the first node of the health network, only a portion of the encrypted sensor data and/or the encrypted patient data, and transmitting the encrypted sensor data and/or the encrypted patient data from the first node of the health network to a second node of the health network. In some examples, the second node may be able to decrypt more of the encrypted sensor data and/or the encrypted patient data than the first node.

In some examples, a root encryption key K may either be provided to the health data sources or negotiated (e.g., via a secure "handshake") between a backend system (such as a provider backend system) and a platform for the health data sources, such as a sensor platform. According to some examples, a group encryption key for top-level access ($KG_1$) may be computed via a one-way hash of the root encryption key. In some such examples, a group encryption key for second-level access ($KG_2$) may be computed via a one-way hash of a group encryption key for top-level access. Likewise, according to some examples, a group encryption key $KG_i$ for any level of access may be computed via a one-way hash of a group encryption key $KG_{i-1}$ for the next higher level of access.

Particular implementations of the subject matter described in this disclosure may be implemented to realize one or more of the following potential advantages. Providing varying degrees of access to health data in a data communication path between health data sources and nodes of a health network may potentially be advantageous because some people (such as health care professionals) may need complete access to the health data sent across the communication path, whereas other people (such as users of a gateway device) may not require access to all the health data sent across the communication path. In some such examples, the "first node" referenced in the preceding paragraph may be a gateway device, such as a gateway device used by a patient. The "second node" may be a device used and/or accessed by a health care professional.

FIG. 1 is a network diagram that shows examples of components of a health network according to some disclosed implementations. An actual health network may include elements not shown in FIG. 1. For example, an actual health network may include many instances of the health data source 105 and the gateway device 115. Some health networks may include more than one provider backend system 125 and/or service platform 120. In this example, a health data source 105 (the "device/tracker/sensor" shown in FIG. 1) is configured to provide data to a cloud-based service platform 120 and a provider backend system 125 via wireless or wired communication with a gateway device 115.

The health data source 105 may be a wearable device having one or more sensors, an implanted device, a therapeutic device a diagnostic device, another type of a medical device, etc. In some examples, the health data source 105 may be configured to provide physiological data, such as body temperature data, respiration rate data, oxygen saturation data, blood glucose data, blood pressure data, heart rate data, data indicating electrical activity of a user's heart, actigraphy data and/or blood alcohol data.

In the example shown in FIG. 1, the health data source 105 provides health data to the gateway device 115 via wireless or wired communication. In this example, the health data is included in one or more encrypted communications 110a. Various types of encrypted communications 110a may be provided by the health data source 105, depending on the particular implementation. In some such implementations, the health data source 105 may be configured to perform one or more functions, such as the encryption of health data, according to instructions and/or information provided by the health data source platform 130. Some examples are described below.

The gateway device 115 (which may also be referred to herein as an "edge platform") may be a smart phone, another type of mobile device, a medical device, etc. According to the example shown in FIG. 1, the gateway device 115 is configured to provide health data to the service platform 120 via one or more encrypted communications 110b. In some examples, the gateway device 115 may be a standalone 2net Hub device that is configured for enabling machine-to-machine (M2M) connectivity between health data sources 105 and one or more devices of the service platform 120. In some implementations, the 2net Hub may be a compact plug-and-play connectivity gateway that includes one or more wired or wireless interfaces (such as short-range radio transceivers) that are configured for collecting health data from medical devices, biometric sensors, etc., and then sending that health data to one or more devices of the service platform 120. In some such examples, the gateway device 115 may send the health data to the service platform 120 via a wide area network (WAN) cellular module. In some alternative examples, the gateway device 115 may be a medical device with one or more wired or wireless interfaces, such as one or more embedded cellular components. In other examples, the gateway device 115 may be a smart phone or another such mobile device that is configured for gateway device functionality such as that disclosed herein.

In some implementations, the gateway device 115 may be configured for gateway device functionality according to instructions (e.g., software) stored on non-transitory media. Such non-transitory media may include memory devices such as those described herein, including but not limited to random access memory (RAM) devices, read-only memory (ROM) devices, etc. In some instances, the instructions may be included in a software application or "app" that has been downloaded to the gateway device 115. The app may, for example, be provided by the service platform 120, the provider backend system 125 or the health data source platform 130.

In some implementations, the service platform 120 of the health network 100 shown in FIG. 1 may be a cloud-based service platform that is implemented via devices of one or more data centers. The devices may include servers, switches, routers, data storage devices, etc. One such device is the node 122, which may be a server, a switch, a router, etc., depending on the particular implementation. According to some implementations, the service platform 120 may provide multiple layers of authentication, encryption and access control. In some examples, the service platform 120 of the health network 100 shown in FIG. 1 may be, or may include, Qualcomm's 2net Platform. Accordingly some implementations of the service platform 120 may be designed to meet specific safety and privacy standards, such as those established according to the Health Insurance Portability and Accountability Act (HIPAA) and/or the Food and Drug Administration.

In the example shown in FIG. 1, the provider backend system 125 is configured to obtain health data originating from one or more health data sources 105 via the service platform 120. According to the example shown in FIG. 1, one or more devices of the service platform 120 (such as the node 122) are configured to provide the health data to the provider backend system via one or more encrypted communications 110c. In some instances, the provider backend system 125 may be a network of devices that is operated by, and/or on behalf of, one or more health care providers. In some examples, the provider backend system 125 may be operated by, and/or on behalf of, a medical group, a hospital, a retail pharmacy, a medical research laboratory, or another health-related entity. The provider backend system 125 may include various devices, which may be wired or wireless devices, mobile devices, desktop devices, etc. One such device is the node 127, which may be a server, a smart phone, a laptop computer, a desktop computer, etc., depending on the particular implementation.

In many instances, the primary data flow within the health network will be from left to right in FIG. 1, from the health data source 105 to the gateway device 115, then to the service platform 120 and then to the provider backend system 125. In some examples, the health data source 105 may include one or more sensors that are configured to provide periodic readings of health data to the gateway device 115. The gateway device 115 may provide some or all of the health data to the service platform 120. The service platform 120 may provide some or all of the health data to the provider backend system 125. In other examples, the readings from the health data source(s) 105 may not be periodic readings.

However, in some implementations some or all of the links within the health network may be configured for two-way communication. For example, the service platform 120 may forward health data upon demand from a node of the provider backend system 125. Thereafter, transmissions of health data from the health data source(s) 105 may be available to one or more authorized users of the provider backend system 125.

Figure 2:
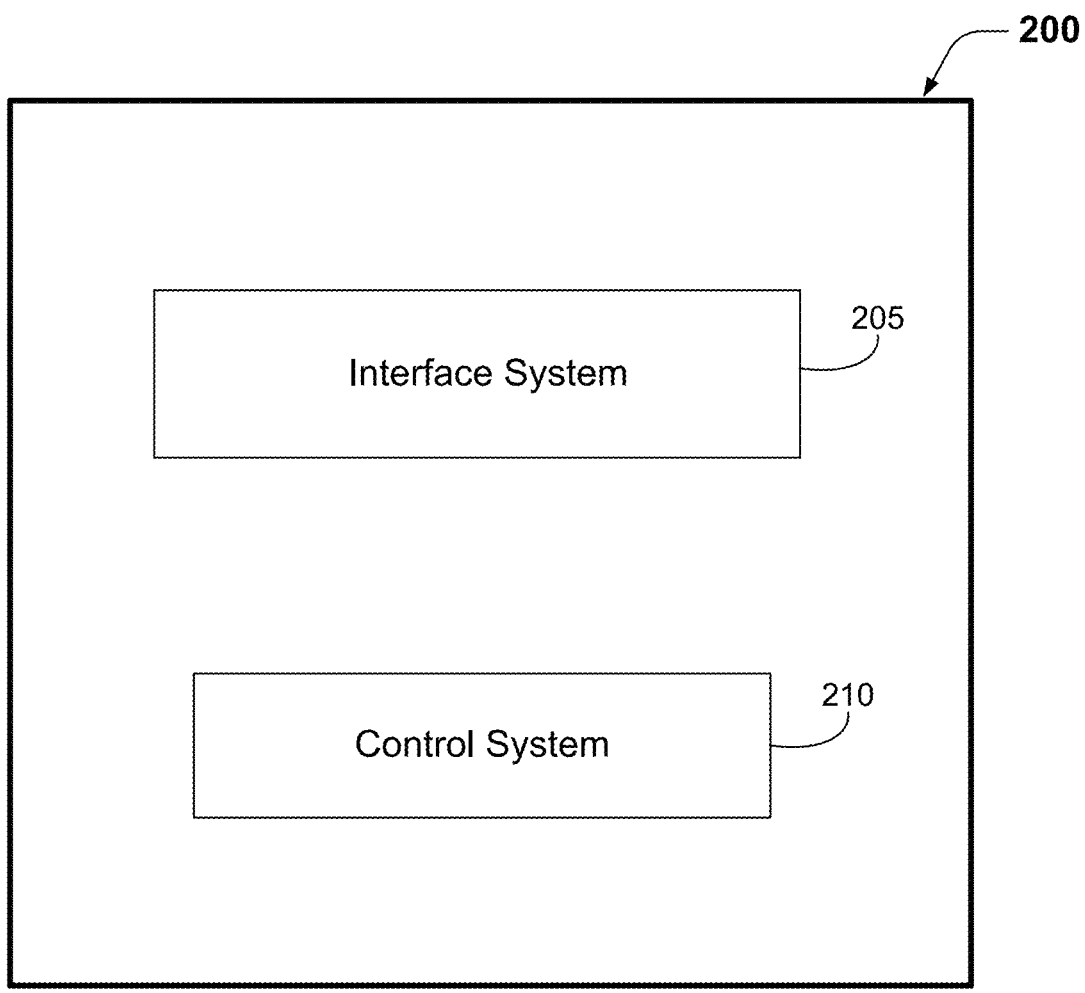
FIG. 2 is a block diagram that shows example components of an apparatus according to some disclosed implementations.

FIG. 2 is a block diagram that shows example components of an apparatus according to some disclosed implementations. The apparatus 200 may, for example, be a node of a health network, such as the health network 100 of FIG. 1. For example, the apparatus 200 may be an instance of a health data source 105, a gateway device 115, a node of the service platform 120 (such as the node 122) or a node of the provider backend system 125 (such as the node 127). In this example, the apparatus 200 includes an interface system 205 and a control system 210. The apparatus 200 may include one or more elements that are not illustrated in FIG. 2. For example, if the apparatus 200 is configured as a health data source 105, the apparatus 200 may include a sensor system including one or more sensors configured for obtaining health data.

In some examples, the interface system 205 may include a wired or a wireless interface system. In some implementations, the interface system 205 may include one or more network interfaces, one or more interfaces between the control system 210 and a memory system and/or one or more interfaces between the control system 210 and one or more external device interfaces (e.g., ports or applications processors).

The interface system 205 may be configured to provide communication (which may include wired or wireless communication, such as electrical communication, radio communication, etc.) between components of the apparatus 200. In some such examples, the interface system 205 may be configured to provide communication between the apparatus 200 and another device, such as a node of the health network 100.

According to some examples, the interface system 205 may be configured to provide communication between the apparatus 200 and other devices and/or human beings. In some such examples, the interface system 205 may include one or more user interfaces. For example, the interface system 205 may include one or more display devices, speakers, microphones, touch and/or gesture detection systems, etc. The interface system 205 may, in some examples, include one or more network interfaces. In some instances, the interface system 205 may include one or more external device interfaces (such as one or more universal serial bus (USB) interfaces). In some implementations, the apparatus 200 may include a memory system. The interface system 205 may, in some examples, include at least one interface between the control system 210 and a memory system.

The control system 210 may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system 210 also may include (and/or be configured for communication with) one or more memory devices, such as one or more random access memory (RAM) devices, read-only memory (ROM) devices, etc. Accordingly, the apparatus 200 may have a memory system that includes one or more memory devices, though the memory system is not shown in FIG. 2.

If the apparatus 200 includes a sensor system, the control system 210 may be capable of controlling the sensor system. The control system 210 may be capable of receiving and processing health data from the sensor system.

In some implementations, functionality of the control system 210 may be partitioned between one or more controllers or processors, such as a dedicated sensor controller and an applications processor. In some implementations, the control system 210 may reside in more than one device. For example, a portion of the control system 210 may reside in one device and another portion of the control system 210 may reside in another device, such as a mobile device (e.g., a smart phone). The interface system 205 also may, in some such examples, reside in more than one device.

As described in more detail below, in some examples the control system 210 may be capable of encrypting and/or decrypting health data. Referring again to FIG. 1, some methods of providing secure data transmission within the health network 100 can provide end-to-end encryption between the health data source(s) 105 and the provider backend system 125. In some such examples, only an authorized user of a device within, or a device that has access to, the provider backend system 125 may be able to decrypt the data.

However, such methods have some drawbacks. For example, it may be desirable to provide at least some degree of access to decrypted data to other elements of the health network, such as the gateway device 115, while data flows from the health data source(s) 105 to the service platform 120 and the provider backend system 125. For example, the gateway device 115 may be a device used by a patient from whom health data is being obtained via the health data source(s) 105. Alternatively, the gateway device 115 may be a device used by the patient's relative, an in-home caregiver, etc.

Figure 3:
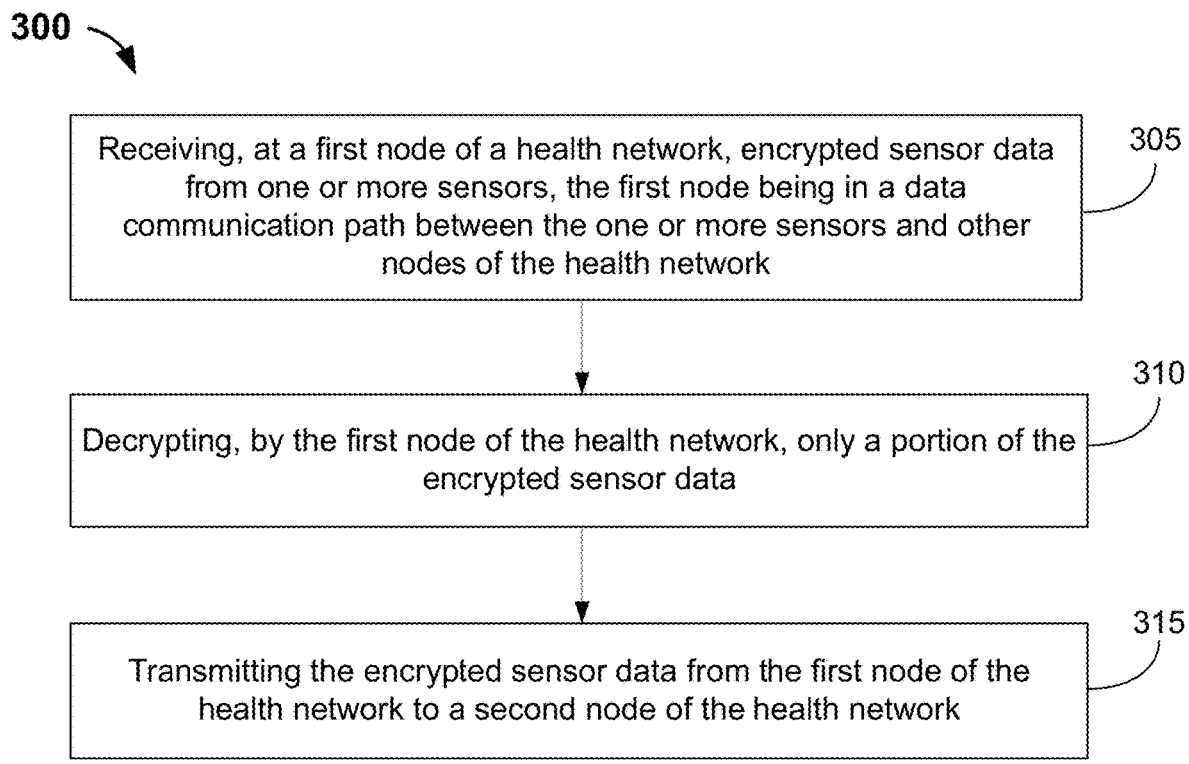
FIG. 3 is a flow diagram that provides examples of operations that may be performed by an apparatus such as the apparatus shown in FIG. 2.

FIG. 3 is a flow diagram that provides examples of operations that may be performed by an apparatus such as the apparatus shown in FIG. 2. The blocks of FIG. 3 (and at least some of the other methods disclosed herein) may, for example, be performed by the apparatus 200 of FIG. 2 or by a similar apparatus. For example, the blocks of FIG. 3 (and the other methods disclosed herein) may be performed, at least in part, by a control system of the apparatus 200. As with other methods disclosed herein, the method 300 outlined in FIG. 3 may include more or fewer blocks than indicated. Moreover, the operations of methods disclosed herein are not necessarily performed in the order indicated.

Method 300 involves controlling access to data in a health network. In this example, block 305 involves receiving, at a first node of the health network, encrypted sensor data from one or more sensors. According to this example, the first node of the health network is in a data communication path between the one or more sensors and other nodes of the health network. A control system of the first node may receive the encrypted sensor data via an interface system of the first node. The first node may, for example, be a gateway device such as the gateway device 115 of FIG. 1. Accordingly, block 305 may involve receipt, via an interface system of the gateway device 115, of encrypted sensor data (or other health data) that is included in one or more encrypted communications 110a from the health data source 105.

In this implementation, block 310 involves decrypting, by the first node of the health network, only a portion of the encrypted sensor data. Here, block 315 involves transmitting the encrypted sensor data from the first node of the health network to a second node of the health network. Referring to FIG. 1, the second node may, for example, be a node of the service platform 120 or a node of the provider backend system 125.

Blocks 310 and 315 may differ according to particular implementations. If, for example, a health data source transmits health data to a service platform via a gateway device, it may be desirable for the gateway device to decode every $N^{th}$ transmission, or at least a portion of every $N^{th}$ transmission. If the health data source transmits a substantial quantity of data in every transmission, it may be desirable for the gateway device to decode only a portion of every $N^{th}$ transmission.

According to some such implementations, the first node may receive a series of encrypted sensor data transmissions from one or more sensors of a health data source. The first node may be configured to decrypt at least a portion of every Nth encrypted sensor data transmission, but not to decrypt first through $(N-1)^{th}$ encrypted sensor data transmissions of the series of encrypted sensor data transmissions.

However, in other examples, the first node may be configured to decode at least a portion of every encrypted health data transmission that is received by the first node. According to some such examples, the first node may receive a series of encrypted sensor data transmissions from one or more sensors. In some implementations, the first node may be configured to decrypt a portion of each encrypted sensor data transmission of the series of encrypted sensor data transmissions.

According to some implementations, a health data source may periodically transmit health data (e.g., every T seconds, every T minutes, etc.). In some such implementations, the first node may receive a series of encrypted sensor data transmissions from the one or more sensors. The first node may decrypt at least a portion of an encrypted sensor data transmission received after a time interval has elapsed but may not decrypt other encrypted sensor data transmissions of the series of encrypted sensor data transmissions received before the time interval has elapsed. The time interval may, in some examples, be selected to include multiple periodic transmissions from a health data source.

Alternatively, or additionally, a health data source may transmit health data upon the occurrence of particular events (e.g., if a patient's blood sugar, blood pressure or other physiological condition is outside a particular range). Such transmissions may, in some examples, include a flag or other indication that the patient's physiological condition is outside the range. In some such examples, the first node may be configured to decode at least a portion of every encrypted health data transmission having an indication that the patient's physiological condition is outside the range.

In some examples, the first node may include a user interface. Method 300 also may involve controlling the user interface to provide one or more indications corresponding to a decrypted portion of the encrypted sensor data. Some such examples may involve controlling a display device to display one or more images corresponding to a decrypted portion of the encrypted sensor data. Alternatively, or additionally, such implementations may involve controlling a speaker to provide audio corresponding to a decrypted portion of the encrypted sensor data.

Figure 4:
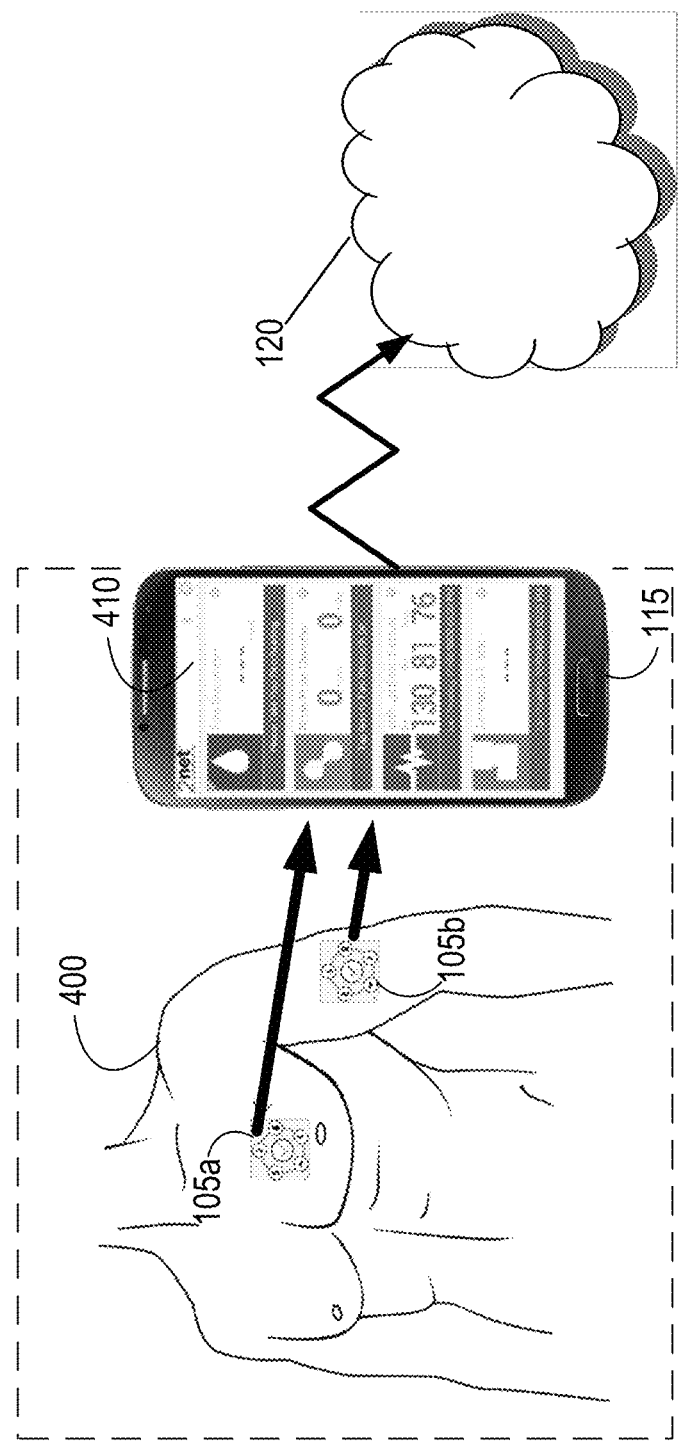
FIG. 4 shows an example of a gateway device configured to provide, via a user interface, one or more indications corresponding to a decrypted portion of the encrypted sensor data.

FIG. 4 shows an example of a gateway device configured to provide, via a user interface, one or more indications corresponding to a decrypted portion of the encrypted sensor data. In this example, the health data sources 105a and 105b are patches that are attached to the body of a patient 400. Here, the health data sources 105a and 105b include a sensor system that is configured to obtain various types of health data, which includes blood glucose data, blood pressure data and heart rate data in this example. In this example, each of the health data sources 105a and 105b includes a control system configured to encrypt the health data and a wireless interface system for transmitting encrypted health data to the gateway device 115.

In this example, the gateway device 115 includes a control system and an interface system. Here, the gateway device 115 is a mobile device and the interface system has a user interface system that includes the display 410. The control system is configured for receiving the encrypted health data from the health data sources 105a and 105b, of decrypting only a portion of the encrypted health data and of transmitting the encrypted health data to a node of the service platform 120.

In the example shown in FIG. 4, the control system of the gateway device 115 is also configured for controlling the user interface to provide one or more indications corresponding to a decrypted portion of the encrypted health data. Here, the display 410 is showing indications of the patient's blood pressure data (130 over 81) and heart rate data (76 beats per minute) corresponding to the decrypted portion of the encrypted health data.

It may be desirable to provide different levels of access for different devices and/or users of a health network. For examples, a person using a gateway device may only need the gateway device to decode a portion of the encrypted health data from a health data source, whereas a health care professional using a device of the provider backend system (or a device that can access the provider backend system) may need to completely decode the encrypted health data. A device of the service platform may, in some examples, have the same level of access as a gateway device. However, in alternative examples, a device of the service platform may have a different (e.g., a lower) level of access than that of a gateway device.

Accordingly, some implementations provide multiple levels of access for different devices and/or users of the health network. For example, some disclosed methods involve providing a plurality of levels of access, by nodes in a data communication path, to encrypted sensor data transmissions from one or more sensors of a health data source 105. Referring again to the method of FIG. 3, in some examples the first node may have a different level of access than the second node. According to some such examples, the second node may have a higher level of access than the first node.

In some implementations, the encrypted sensor data from the one or more sensors may include a first portion encrypted at a first level and a second portion encrypted at a second level that is different from the first level. A particular node may be able to decrypt both the first portion and the second portion, or only one of the portions, depending on the level of access granted to the node.

In some examples, a group encryption key for top-level access ($KG_i$) may be computed via a one-way hash of a root encryption key. According to some such examples, a group encryption key $KG_i$ for an $i^{th}$ level of access may be computed via a one-way hash of a group encryption key $KG_{i-1}$ for an $(i-1)^{th}$ level of access. The group encryption key $KG_i$ and the group encryption key $KG_{i-1}$ may be symmetrical encryption keys.

According to some examples, group encryption keys $KG_1$ for top-level access to data of the health network may be computed via a one-way hash of the root encryption key, as follows:

$$KG_1 = \text{hash}(K)$$

In some such examples, the group encryption keys $KG_1$ may be generated by a device, such as a server of the service platform 120, a server of the provider backend system 125 or a server of the health data source platform 130. The server may provide the group encryption keys $KG_1$ to devices used by top-level users, such as devices used by health care professionals. Alternatively, the root encryption key K and the hash function may be provided to devices used by top-level users and these devices may generate the group encryption keys $KG_1$.

In some examples, group encryption keys $KG_2$ for second-level access to data of the health network may be computed via a one-way hash of the group encryption keys $KG_1$, as follows:

$$KG_2 = \text{hash}(KG_1)$$

Likewise, according to some examples, a group encryption key $KG_i$ for any level of access may be computed via a one-way hash of a group encryption key $KG_{i-1}$ for the next higher level of access, as follows:

$$KG_i = \text{hash}(KG_{i-1})$$

In some implementations, the group encryption keys are symmetric keys. In other words, a data transmission may be encrypted or decrypted using the same group encryption key. For example, the health data source may produce encrypted cipher text Ci as follows:

$$Ci = \text{Enc}(Pi)KG_i,$$

wherein Pi represents unencrypted plaintext.

In some instances, these calculations may be performed by a server and/or by the health data source, e.g. by a control system of the health data source. According to some such examples, a control system of a health data source may be configured to receive a root encryption key K and to compute at least a group encryption key $KG_i$ for top-level access via a one-way hash of the root encryption key. In some such examples, one or more devices of a service platform or a provider backend system may be configured to provide, or cause to be provided, the root encryption key K to the health data source. According to some such examples, the root encryption key K may be negotiated (e.g., via a secure "handshake") between a health data source and another device, such as a device of a service platform, a device of a provider backend system or another device.

Referring again to FIG. 1, in this example one or more devices of the service platform 120 and/or the provider backend system 125 may be configured for communication with the health data source platform 130. The health data source platform 130 may include one or more servers that are configured to provide instructions and/or information to health data sources 105. A health data source 105 may be configured to perform one or more functions, such as the encryption of health data, according to instructions and/or information provided by the health data source platform 130. For example, the health data source platform 130 may provide the root encryption key K to the health data source 105 upon instruction from a device of the service platform 120 or the provider backend system 125. In some instances, the instructions and/or information may be provided to the health data source 105 via the gateway device 115.

In some examples a hash function may be distributed to users or nodes having one or more access levels, along with a group encryption key. For example, using the hash function and a group encryption key $KG_i$ for any level of access, the devices of such users can generate the group encryption keys of access levels that are lower in privilege (higher in number, such as $KG_{i+1}$, $KG_{i+2}$, etc.) using the hash function.

In some implementations, if a transmission is encrypted by group encryption key $KG_1$, then users of access level 1 (the top level) can decode the transmission but users of access level 2 (the second level) and below cannot. Similarly, in some examples if a message is encrypted by group encryption key $KG_2$, then users of access levels 1 and 2 can decode the message but users of access level 3 or below cannot.

According to some examples, an encrypted data transmission may indicate the minimum access level required to decrypt at least part of the data transmission. In some implementations, an encrypted data transmission may have some portions encrypted at one level (e.g., the top level) and other parts encrypted at another level (e.g., the $2^{nd}$ level).

In some implementations, there may be an "app" provided by the health provider that can pull data from the provider backend over a network, which may be different from the health network that is shown in FIG. 1. Some such examples may also involve multiple levels of access to such data. The access may, in some instances, be controlled according to various group encryption keys as described herein. It is to be noted that there could be additional hop-by-hop encryption (e.g., between the different nodes shown in FIG. 1) that could use symmetric or asymmetric cryptography. This additional encryption would be in addition to (on top of) the layered encryption scheme described above.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

The invention claimed is:

1. A method of controlling access to data in a health network, the method comprising:
   receiving, at a first node of the health network, a series of encrypted sensor data transmissions from one or more sensors configured to provide physiological data of a user, the first node being in a data communication path between the one or more sensors and other nodes of the health network;
   decrypting, by the first node of the health network, a portion of the encrypted sensor data transmissions to generate unencrypted clear, plain data, wherein the portion is less than the entire received encrypted sensor data transmissions;

displaying, in response to decrypting the portion of the encrypted sensor data transmissions, on a graphical user interface of the first node, one or more images corresponding to the unencrypted data including at least a portion of the provided physiological data of the user; and transmitting the encrypted sensor data transmissions from the first node of the health network to a second node of the health network.

2. The method of claim 1, wherein the first node of the health network is a gateway device.

3. The method of claim 1, further comprising:
providing, via a speaker of the first node, audio corresponding to the decrypted portion of the encrypted sensor data transmissions.

4. The method of claim 1, wherein the second node of the health network is a node of a health service provider system.

5. The method of claim 1, wherein the method involves providing a plurality of levels of access, by nodes in the data communication path, to the encrypted sensor data transmissions from the one or more sensors.

6. The method of claim 5, wherein the first node has a different level of access than the second node.

7. The method of claim 6, wherein the second node has a higher level of access than the first node.

8. The method of claim 5, wherein a group encryption key for top-level access ($KG_t$) is computed via a one-way hash of a root encryption key.

9. The method of claim 8, wherein a group encryption key $KG_i$ for an $i^{th}$ level of access is computed via a one-way hash of a group encryption key $KG_{i-1}$ for an $(i-1)^{th}$ level of access.

10. The method of claim 9, wherein the group encryption key $KG_i$, and the group encryption key $KG_{i-1}$ are symmetrical encryption keys.

11. The method of claim 1, wherein the encrypted sensor data transmissions from the one or more sensors includes a first portion encrypted at a first level and a second portion encrypted at a second level that is different from the first level.

12. The method of claim 1, wherein the first node decrypts at least a portion of every Nth encrypted sensor data transmission and does not decrypt any of a first through $(N-1)^{th}$ encrypted sensor data transmissions of the series of encrypted sensor data transmissions.

13. The method of claim 1, wherein the first node decrypts at least a portion of an encrypted sensor data transmission received after a time interval has elapsed but does not decrypt other encrypted sensor data transmissions of the series of encrypted sensor data transmissions received before the time interval has elapsed.

14. The method of claim 1, wherein the first node decrypts a portion of each encrypted sensor data transmission of the series of encrypted sensor data transmissions.

15. An apparatus configured to function as a first node of a health network, the first node being in a data communication path between a one or more sensors configured to provide physiological data of a user and other nodes of the health network, the apparatus comprising:
an interface system configured for receiving a series of encrypted sensor data transmissions from the one or more sensors; and
a control system configured to:
receive, from the interface system, the series of encrypted sensor data transmissions;
decrypt a portion of the encrypted sensor data transmissions to generate unencrypted clear, plain data, wherein the portion is less than the entire received encrypted sensor data transmissions;
provide, to a display of the apparatus, in response to decrypting the portion of the encrypted sensor data transmissions, one or more images corresponding to the unencrypted data including at least a portion of the provided physiological data of the user; and
cause the interface system to transmit the encrypted sensor data transmissions to a second node of the health network.

16. The apparatus of claim 15, wherein the apparatus is a gateway device of the health network.

17. The apparatus of claim 15, wherein the control system is further configured to provide, to a speaker of the apparatus, audio corresponding to the decrypted portion of the encrypted sensor data transmissions.

18. The apparatus of claim 15, wherein the second node of the health network is a node of a health service provider system.

19. The apparatus of claim 15, wherein the control system is configured to decrypt at least a portion of every Nth encrypted sensor data transmission, and wherein the control system is configured not to decrypt any of a first through $(N-1)^{th}$ encrypted sensor data transmissions of the series of encrypted sensor data transmissions.

20. The apparatus of claim 15, wherein the control system is configured to decrypt at least a portion of an encrypted sensor data transmission received after a time interval has elapsed, and wherein the control system is configured not to decrypt other encrypted sensor data transmissions of the series of encrypted sensor data transmissions received before the time interval has elapsed.

21. The apparatus of claim 15, wherein the control system is configured to decrypt a portion of each encrypted sensor data transmission of the series of encrypted sensor data transmissions.

22. A non-transitory medium having instructions for controlling a first node of a health network to perform a method stored thereon, the first node being in a data communication path between one or more sensors configured to provide physiological data of a user and other nodes of the health network, the method comprising:
receiving, at the first node of the health network, a series of encrypted sensor data transmissions from the one or more sensors;
decrypting, by the first node of the health network, a portion of the encrypted sensor data transmissions to generate unencrypted clear, plain data, wherein the portion is less than the entire received encrypted sensor data transmissions;
displaying, in response to decrypting the portion of the encrypted sensor data transmissions, on a graphical user interface of the first node, one or more images corresponding to the unencrypted data including at least a portion of the provided physiological data of the user; and
transmitting the encrypted sensor data transmissions from the first node of the health network to a second node of the health network.

23. The non-transitory medium of claim 22, wherein the first node of the health network is a gateway device.

24. The non-transitory medium of claim 22, further comprising:
providing, via a speaker of the first node, audio corresponding to the decrypted portion of the encrypted sensor data transmissions.

25. The non-transitory medium of claim 22, wherein the method involves providing a plurality of levels of access, by nodes in the data communication path, to the encrypted sensor data transmissions from the one or more sensors.

26. The non-transitory medium of claim 22, wherein the first node decrypts at least a portion of every Nth encrypted sensor data transmission and does not decrypt any of a first through $(N-1)^{th}$ encrypted sensor data transmissions of the series of encrypted sensor data transmissions.

27. The non-transitory medium of claim 22, wherein the first node decrypts at least a portion of an encrypted sensor data transmission received after a time interval has elapsed but does not decrypt other encrypted sensor data transmissions of the series of encrypted sensor data transmissions received before the time interval has elapsed.

28. The non-transitory medium of claim 22, wherein the first node decrypts a portion of each encrypted sensor data transmission of the series of encrypted sensor data transmissions.

29. An apparatus configured to function as a first node of a health network, the first node being in a data communication path between a one or more sensors configured to provide physiological data of a user and other nodes of the health network, the apparatus comprising:
- means for receiving, at the first node of the health network, a series of encrypted sensor data transmissions from the one or more sensors;
- means for decrypting, by the first node of the health network, a portion of the encrypted sensor data transmissions to generate unencrypted clear, plain data, wherein the portion is less than the entire received encrypted sensor data transmissions;
- means for displaying, in response to decrypting the portion of the encrypted sensor data transmissions, one or more images corresponding to the unencrypted data including of at least a portion of the provided physiological data of the user, and
- means for transmitting the encrypted sensor data transmissions from the first node of the health network to a second node of the health network.

30. The apparatus of claim 29, further comprising:
- means for providing audio corresponding to the decrypted portion of the encrypted sensor data transmissions.

* * * * *